US006184397B1

(12) United States Patent
Roden et al.

(10) Patent No.: US 6,184,397 B1
(45) Date of Patent: Feb. 6, 2001

(54) PREPARATION OF STEROL AND STANOL-ESTERS

(75) Inventors: Allan Roden, Noblesville, IN (US); James L. Williams, Reynoldsburg, OH (US); Ruey Bruce, Columbus, OH (US); Frank Detrano, Lancaster, OH (US); Marie H. Boyer; John D. Higgins, III, both of Fort Washington, PA (US)

(73) Assignee: McNeil-PPC, Inc., Skillman, NJ (US)

( * ) Notice: Under 35 U.S.C. 154(b), the term of this patent shall be extended for 0 days.

(21) Appl. No.: 09/336,773

(22) Filed: Jun. 21, 1999

Related U.S. Application Data

(63) Continuation-in-part of application No. 09/211,978, filed on Dec. 15, 1998, which is a continuation-in-part of application No. 09/139,460, filed on Aug. 25, 1998, now Pat. No. 5,892,068.

(51) Int. Cl.$^7$ ........................................................ C07J 9/00
(52) U.S. Cl. ............................................................ 552/200
(58) Field of Search .............................................. 552/554

(56) References Cited

U.S. PATENT DOCUMENTS

| | | | |
|---|---|---|---|
| 4,309,448 | 1/1982 | Takaishi et al. | 424/365 |
| 4,393,044 | 7/1983 | Takada et al. | 424/59 |
| 4,428,885 | 1/1984 | Higaki et al. | 260/410.9 |
| 5,556,970 | 9/1996 | Kawasaki et al. | 554/190 |
| 5,892,068 | * 4/1999 | Higgin, III | 552/554 |
| 5,958,913 | 9/1999 | Meittenen et al. | 514/182 |
| 6,031,118 | 2/2000 | van Amerongen et al. | 552/544 |

FOREIGN PATENT DOCUMENTS

| | | | |
|---|---|---|---|
| 0 897 970 A1 | 2/1999 | (EP) | C11C/3/10 |
| 0 911 385 a1 | 4/1999 | (EP) | C11C/3/00 |
| 44004974B | 8/1965 | (JP) . | |
| WO 95/00158 | 1/1995 | (WO) | A61K/37/00 |
| WO 97/24420 | 7/1997 | (WO) | C11C/1/02 |
| WO 97/26804 | 7/1997 | (WO) | A23L/1/30 |
| WO 99/30569 | 6/1999 | (WO) | A23D/7/00 |
| WO 99/39715 | 8/1999 | (WO) | A61K/31/56 |
| WO 99/43218 | 9/1999 | (WO) | A23L/1/30 |
| WO 99/59423 | 11/1999 | (WO) | A23D/9/00 |

OTHER PUBLICATIONS

"Effect of Plant Sterol Esters on the Absorption of Dietary Cholesterol", The Procter & Gamble Company, Mattson, Volpenhein & erickson, J. Nutr. 107, pp. 1139–1146, (1977).
"Optimizing the Effect of Plant Sterols on cholesterol Absorption in Man", Mattson, Grundy, & Crouse, The American journal of Clinical Nutrition 35: Apr. 1982; pp. 697–700.
M. van Dam; D. van Schuppen; American Perfume and Cosmetics, "New Lanolin Acid Esters", vol. 84, No. 8, 1969, pp. 37–40.

\* cited by examiner

*Primary Examiner*—Raymond Henley, III

(57) ABSTRACT

The present invention provides a method for the direct esterification of stanols and sterols with catalyst, which can be acidic or basic, in the presence of a color deactivating agent to form stanol/sterol-esters. The method provides a synthetic route that is amenable to large scale production of the esters in high yields. A preferred embodiment employs a food grade process free of organic solvents or mineral acids.

20 Claims, No Drawings

PREPARATION OF STEROL AND STANOL-ESTERS

RELATED APPLICATIONS

This application is a continuation-in-part of U.S. Ser. No. 09/211,978 filed on Dec. 15, 1998; which is a continuation-in-part of U.S. Ser. No. 09/139,460 filed on Aug. 25, 1998; now U.S. Pat. No. 5,892,068; the contents of all hereby incorporated by reference as if set forth in their entirety.

FIELD OF THE INVENTION

This invention relates to the preparation of discrete sterol and stanol-esters through a highly efficient catalyzed route in the presence of a color deactivating agent.

BACKGROUND OF THE INVENTION

It has been shown that the addition of plant sterols, such as β-sitosterol, to diets will reduce serum cholesterol levels. The sterols reduce serum cholesterol through the disruption of intestinal absorption of dietary cholesterol by displacing it from bile acid micelli. More recently, β-sitosterol's saturated derivative, β-sitostanol, has been shown to be more effective in the reduction of intestinal cholesterol absorption. The sitostanol itself is virtually unabsorbed, so it does not contribute at all to in vivo serum sterol concentration upon consumption. Unfortunately, typical sterols and stanols are insoluble in the micelli phase of the alimentary canal and have only limited solubility in oils and/or fats or water. Hence, free sterols or stanols themselves are not optimum candidates for use in typical pharmaceutical or dietary dosage forms as cholesterol reducing agents.

U.S. Pat. No. 5,502,045 discloses the interesterification of stanols with a fatty acid ester from an edible oil to produce a waxy sterol-ester mixture with improved fat solubility characteristics. Specifically, this patent discloses the reaction of sitostanol interesterified with fatty acids from methyl esters of an edible oil such as rapeseed oil specifically via a base catalyzed transesterification reaction. This is a process that is widely used in the food industry. From a pharmaceutical standpoint, however, interesterification processes such as this have some distinct disadvantages. Primarily, the composition profile of the sterol-ester products are difficult to control since the profile is dependent on the array of fatty acids present in the edible oil employed in the reaction. In addition methanol a by-product of this reaction must be carefully removed and the use of methyesters requires large excesses to be used making recycle difficult.

In a different approach, German Patent 2035069 discloses the esterification of sterol-esters to fatty acids via a non-food grade process. In particular, thionyl chloride is employed as a reactant which when reacted forms HCl gases as a by-product. Such techniques are not suitable for the production of food grade materials, and they are undesirable in general.

Japanese Patent 76-11113 discloses a catalyst free esterification of higher fatty acid esters of sterols or related vitamins. However this process employs a significant molar excess of fatty acid, a minimum of 25% up to 50%, which in turn requires the use of an alkali refining process to recover the ester product. The stoichiometric excess fatty acid and the isolation techniques result in a products that are discolored.

From a pharmaceutical standpoint, there is an unmet need for a method for the synthesis of discrete stanol/sterol-esters via a bulk food grade process. Discrete compounds are more desirable than mixtures for three main reasons: 1) the composition and performance specifications can be controlled better; 2) structure/activity studies are more feasible; and 3) the physicochemical and chemical properties can be controlled. These advantages of discrete stanol/sterol-esters will be elaborated on later.

In addition there is a need for food grade esters of sterols/stanols which are light in color food preparation of appealing food products. Also processes that reduce processing losses and equipment costs are needed.

SUMMARY OF THE INVENTION

The present invention comprises a method for the direct esterification of stanols or sterols with catalysts, in the presence of a color deactivating agent to form discrete stanol/sterol-esters. The catalyst can be either a weak acid in the classic sense, or a Lewis acid, or traditional basic materials. The method provides a synthetic route that is amenable to large scale production of the stanol-esters in high yield and purity by a food grade process that in a preferred embodiment is free of organic solvents or mineral acids and produces limited by-products. The method ultimately provides a convenient process that enables one to design discrete stanol/sterol-esters with various physical and biological properties.

DETAILED DESCRIPTION OF THE INVENTION

The present invention provides the direct esterification of stanols and sterols through the reaction of the stanol/sterol and fatty acids using either acid or basic catalyst. β-sitostanol, the most preferred starting material, is commercially produced from β-sitosterol by a hydrogenation reaction and is commercially available, from various sources including Raisio Corporation.

The acids, which include the associated salts, reacted in the present invention contain from about 4 to about 24 carbon atoms. The acids include saturated acids, but are preferably unsaturated acids, including polyunsaturated acids.

The saturated fatty acids reacted in the present invention are of the formulae $CH_3—(CH_2)_n—CO_2H$ wherein n is an integer of from 2 to 22, preferably n is from about 12 to about 20. The term fatty acid is well known and understood to those with skill in the art, see for example, *Hawley's Condensed Chemical Dictionary*, Eleventh edition. The term includes acids themselves and salts of these acids. The fatty acids include saturated acids, such as stearic, butyric, lauric, palmitic and the like. Unsaturated fatty acids, including polyunsaturated fatty acids can also be used in the present invention. Suitable unsaturated fatty acids include oleic, linoleic, linolenic, docosohexanoic acid, conjugated linoleic acid and the like. As disclosed in U.S. Pat. No. 5,554,646, column 1, lines 44–48, conjugated linoleic acid is 9,11-octadecadienoic acid, 10,12-octadecadienoic acid, and mixtures thereof. The present invention includes both straight and branched acids, with straight chain acids being preferred.

In the present invention the sterol and stanol-esters have the general formula depicted as FIG. I:

Figure I

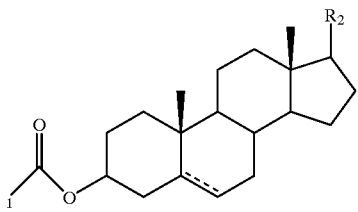

wherein $R_1$ is understood to include aliphatic straight or branched carbon chains having a length of about $C_3$–$C_{24}$, preferably from $C_6$–$C_{22}$ and most preferably $C_{12}$–$C_{21}$ groups, and $R_2$ is understood to include aliphatic straight or branched carbon chains ranging $C_3$–$C_{15}$, preferably $C_6$–$C_{12}$, and most preferably, $C_9$ groups. More preferably, $R_2$ is selected from the group ($C_1$–$C_{12}$) alkyl, ($C_1$–$C_8$) alkoxy, ($C_2$–$C_8$) alkenyl, ($C_2$–$C_8$) alkynyl, ($C_3$–$C_8$) cycloalkyl, halo ($C_2$–$C_8$) alkenyl, halo ($C_2$–$C_8$) alkynyl) where halo is understood to include chloro, fluoro, bromo, iodo and the like. Alkyl includes both straight and branched chain groups of carbon atoms. Typical alkyl groups include methyl, ethyl, n-propyl, isopropyl, n-butyl, sec-butyl, isobuytyl, t-butyl, n-pentyl, neopentyl, isopentyl, hexyl, heptyl and the like. The alkyl groups may be halogenated with one, two three or more halogen atoms.

The terms alkenyl and alkynyl included branded and straight chain hydrocarbons having at least one unsaturated bond.

Unsaturation at $C_5$ provides the corresponding sterol-ester. Any stanol or sterol that is functionalized with a hydroxy group is suitable for esterification by the process described herein. Provided below is a generic formula of the stanol/sterols that can be esterified in the present invention:

Figure II

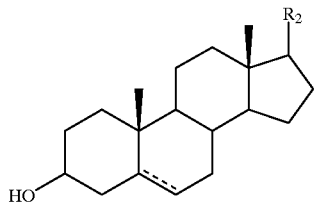

$R_2$ is understood to have the same meaning as set forth above.

Stanols that are capable of being esterified in the present invention include, but are not limited to β-sitostanol, (depicted in FIG. III below), as well as other related compounds including cholestanol, ergostanol, brassicastanol, avenastenol, alpha-amyrin, cyclartenol, lupenol and the like.

Figure III

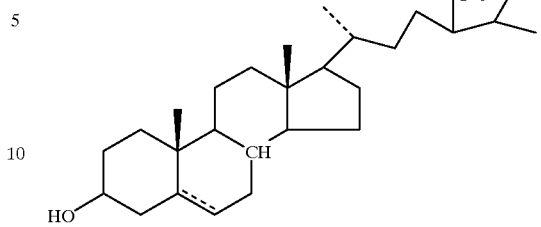

For example, this process is also amenable to sterols such as □□sitosterol (unsaturated at $C_5$, as shown in FIG. III above).

The molar ratios of the starting materials for the esterification reaction, notably the stanol/sterol and the fatty acid, are provided in stoichiometric levels. In a highly preferred embodiment, the fatty acid is present in a 5–10% excess so as to react all of the stanol. Any excess unreacted fatty acid is easily removed in the product workup.

Any suitable catalyst can be employed in the present invention. The catalyst can be weak acids, a Lewis acid, or a basic catalyst. Suitable acid catalysts are disclosed in U.S. Pat. No. 5,892,068 hereby incorporated by reference. Suitable acid catalysts include toluene sulfonic acid, methane sulfonic, sodium hydrogen phosphate, sodium bisulfate, although mineral acids are not preferred. Suitable catalyst that may be acting as a Lewis acid include, iron chloride, iron oxide, magnesium oxide, manganese oxide, manganese chloride, sodium hydroxides, nickel chloride, tin oxide, tin chloride, as well as zinc oxide and zinc chloride. Some basic materials act as a catalyst for this reaction as well such as sodium hydroxide. The catalyst are typically sufficient if provided at a 1 mole percent as compared to the level of reactants. As used herein Lewis acid catalysts are understood to be compounds which are potential electron-pair acceptors. The level of catalyst can be increased or decreased to provide the reaction rate desired, however, if too much catalyst is provided a higher than desired level of side reaction and products may result. Other suitable Lewis acid catalysts include boron trifluoride, aluminum chloride, and the like. Any suitable Lewis acid can function as the catalyst, with zinc oxide being the preferred catalyst. The catalyst can be in the form of a solid, liquid or gas.

One of the most effective aspects of the present invention is that the reaction is performed neat, wherein no solvents are added to the reaction mixture, because the acid, in a preferred embodiment a fatty acid in a molten state, acts as both a reactant and solvent.

It is particularly appropriate to run the neat reactions under vacuum in order to remove water from the reaction mixture thereby driving the reaction to completion and increasing the yield of the desired ester. As the water is not soluble in the product phase much lower levels of fatty acids are required to drive the reaction to completion.

The reaction temperature is conducted at temperatures from about 75 to about 225° C. The preferred range is from about 100 to about 220° C. and most preferably from about 140 to 180° C. The reaction period may vary widely, but for best results and economy the reactions should be allowed to run to completion. Reaction times of greater than 12 hours are common but not necessarily required. One advantage of the present invention is the high yield of the ester product provided by the process. The present process provides yields of greater than 90% and preferably greater than 95%.

The reaction of the present invention is sufficiently mild to prepare esters that were not capable of being synthesized using methods previously disclosed in the art. In particular, the present invention provides a method for preparing esters which are the reaction product of DHA (cis-4,7,10,13,16, 19-docosahexeanoic acid) and CLA (octadecadienoic acid) and the sterol/stanol set forth above. These products are of particular interest in that both DHA and CLA have been reported to possess cholesterol-lowering characteristics. Therefore, a compound which contains the combination of both the stanol or sterol with a pendent ester functionality which when hydrolyzed provides another cholesterol-limiting agent would be highly beneficial. The combination of these functions would be beneficial in that it is reported that the DHA and CLA lower cholesterol in the body by different mechanisms than do sterol and stanol products.

The ester products of CLA and the sterol/stanol are provided below:

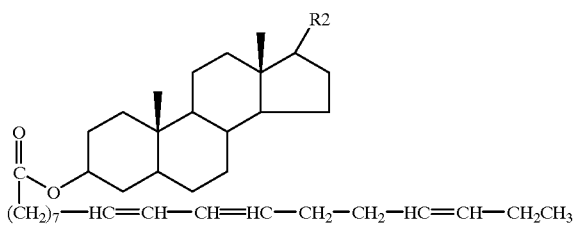

sterol/stanol octadecadienoate; the 9,11-octadecadienoic form is depicted above, and the 10,12 isomer is also common.
More preferably,

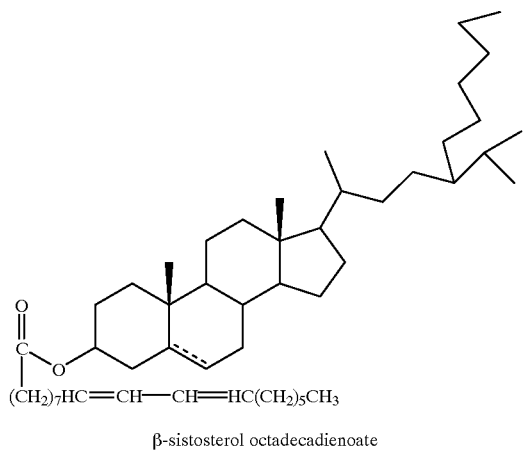

β-sistosterol octadecadienoate

Similarly, the ester product of DHA and sterol/stanol are provided below:

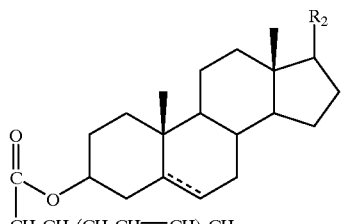

Sterol/stanol docosahexaenoate, and more preferably

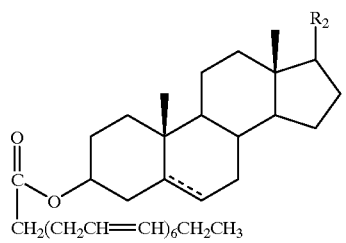

β-sitosterol docosahexaenoate; and
β-sitostanol docosahexaenoate

The present invention also provides a method for reducing serum cholesterol an effective amount of CLA and DHA esters to reduce serum cholesterol. Typically, the level is from about 1 to about 20 g/day, preferably from about 3 to about 15, and most preferably from about 6 to about 9 per day.

Three isolation techniques as described below can be used to isolate the ester reaction product.

Method A: An aqueous/organic solvent extraction isolation may be employed to recover the stanol-ester. Typical organic solvents include dichloromethane, chloroform or toluene. A typical aqueous/organic workup was employed where the ester was extracted into an organic solvent and subsequently isolated after evaporation. For example, the reaction mixture is cooled to room temperature followed by addition of $CH_2Cl_2$. The solution was then washed several times with aqueous $NaHCO_3$. The fatty acid salts are partitioned into the aqueous phase and can easily be removed. The remaining organic phase containing the isolated ester is then dried over anhydrous $NaSO_4$ and decolorized with activated charcoal. When light, non-chlorinated organic solvents (i.e., hexane) are used for extraction, the formation of an inseparable emulsion is observed. Pure esters were recovered as white solids or oils after removal of the solvent on a rotary evaporator and subsequent cooling.

Method B: In a prefered isolation techniques used when the reaction is catalyzed with a weak acid an amount of sodium hydroxide at least equal to but not more than a 10% molar excess of the acid used is added to the esters dissolved in 10–15% water based on the reaction mixture is added. After gentle mixing the water and soaps are allowed to drain off. The material is then bleached and deodorized by procedures common to the edible oil industry. As most of the excess fatty acids will remain in ester product after washing they will be recovered and recycled from the deodorizer.

Method C: In a more preferred isolation technique used for basic catalysts and some Lewis acid catalysts, the ester reaction product is isolated using only water. The crude reaction mixture is washed with 10% water that was allowed to separate for 1 to 2 hours and then drained off. The resultant ester is then bleached with edible oil bleaching clay or silca based bleaching aids to remove color and traces of soap present and deodorized to remove excess fatty acids which are ready for recylce without further processing.

Although all three methods produced esters identical in purity, the recovered yields (>96%) were better with Method C. This method is also more amenable to large scale synthesis because it gives high purity product without the use of hazardous non-food grade solvents. This method also has fewer interactions with the raw materials which results in improved yield and reduced product losses. Method B is preferred to A as it also provides improved yields when compared to A. Both Method B and C allow easier recycle of excess fatty acids reducing product costs.

The present invention provides several advantages over previous disclosed processes. The present invention provides a method to synthesize substantially discrete stanol-esters rather than mixtures of stanol-esters. As used herein, substantially discrete is understood to mean that the reaction product, the desired ester is provided in a very high proportion of the reaction product. Typically the desired ester is provided in the reaction product in at least 90 percent by weight, more preferably in an amount at least about 98 percent and if the reaction is allowed to run to completion to at least 99 percent by weight. The present invention is capable of providing essentially a single stanol (sterol)-ester, with less than 0.2 weight percent of other ester products. The previously disclosed interesterification processes provide a mixture of the stanol-ester products. For example, the previously disclosed processes provide mixtures of stanol-esters, often with broad ranges of the stanol-esters present (for example, a mixture of 4 esters in ratios of 30, 30, 20, 20 percent by weight). Also in comparison, the previously disclosed direct esterification processes use hazardous, deleterious reagents.

This production of discrete stanol/sterol-esters has several important advantages over the stanol/sterol-ester mixtures produced by other processes. Firstly, tighter performance specifications (i.e., melting point, specific gravity structural species purity) are possible for discrete compounds. This is because the properties of discrete compounds can be controlled with more precision than for mixtures. Hence, proper performance characteristics and quality of discrete esters are more easily assured as compared to a mixture of ester products.

Furthermore, because the present invention provides the synthesis of discrete stanol/sterol-esters, structure/activity relationships over a range of fatty acid chain lengths can be ascertained. The determination of structure/activity relationships, which are fundamental to rational drug development, are only feasible when screening discrete compounds.

The gross physical and physiologic properties of the sterol/stanol-ester can be controlled since those properties are dependent upon which fatty acid is employed. For example, esterification to unsaturated fatty acids (i.e., oleic acid) can lead to low melting solids or even liquid products, whereas saturated fatty acid analogs (i.e., stearic acid) tend to lead to higher melting free flowing solids. This ability to so extensively manipulate the physical properties of a high melting sterol is quite unexpected.

The present invention allows the selection of the ester to match the physical properties which are desired. The solid free flowing material is desirable for the manufacture of compressed tablets, or the incorporation of the stanol-ester into baking products. These oil-like stanol/sterol-esters are advantageously employed in the manufacture of soft gel dosage forms or incorporated into a salad dressing or yogurt.

A further advantage of the present invention is the ability to add a suitable amount of a color deactivating agent during the reaction. Typically the amount of the color deactivating agent is from about 0.05% to about 1% weight percent based upon the reaction total weight; preferably from about 0.15 to about 0.5%; and most preferably from about 0.25 to about 0.35 weight percent. Suitable color deactivating agents include carbon, charcoal and carbon black; edible oil, bleaching earth, or a silica bleaching such as Trisil from Grace Chemical, of which charcoal or activated carbon is preferred. The color deactivating agent prevents the reaction product from becoming discolored, i.e., not white and the color deactivating agent is preferably incorporated with either the stanol/sterol and acid in the reaction vessel.

The resulting product of the present invention is white, free from off flavors and other volatile material with a bland flavor. The resulting stanol ester/sterol-ester product has a Gardner color value of less than 8, typically less than about 6, preferably less than about 4 and most preferably less than about 3 on the Gardner color scale. The Gardner color scale is known to those in the art. The product of the reaction are formed into a block and the color block is compared to samples of a predetermined color. Earlier processes provided product with higher color values. For example, the stanol esters produced in accordance with U.S. Pat. No. 5,892,068, had a Gardner color value of from about 9 to about 12. Using the process described in Japanese Patent 76-11113, the products would have Gardner color values of from about 10 to about 12.

The reaction product can be dissolved in oil and added to any food product that contains an oil component.

Another advantage of the present invention is the elimination of the need for excessive soaps during the washing of the product to deactivate or remove any catalyst that may be contained in the resulting product. This improves the yield reducing loss and speeding the time for reactor turn over. A further advantage of the reaction is the ease of recycle of excess fatty acids without further processing.

Another advantage of the present invention is the production of a lower color product. A further advantage of the present invention is the use of low excess of fatty acids. In other disclosures large excesses of the fatty acid source are needed to drive the reaction to completion (often a molar ratios of two fatty acids to one stanol/sterol). This makes the clean up, or processing after the reaction difficult and expensive. The use of large excess reduces the quantity of product made in a given reactor increasing capital cost and increasing labor cost per pound of product.

Yet another advantage of the present invention is the faster reaction times provided by the catalyzed reactions as compared to the uncatalyzed reactions when conducted at the same reaction temperature. In addition to shorter reaction times, the resulting product also has better color. For example, uncatalyzed reactions conducted at 250° C. have reaction times of greater than 13 hours. However, the catalyzed reaction, carried out under similar conditions such as batch size and reactor geometry, can be conducted at a much lower temperature, 170° C. and have reaction times to completion of 13 hours. Generally reaction times of the present invention range from about 8 to about 15 hours, preferably 10 to about 14 and most preferably from about 12 to about 13 hours.

The term acid used herein to describe acid used as a reactant is understood to include fatty acids, saturated including polyunsaturated and polyunsaturated acids as is set forth herein. The following examples are provided to further illustrate the claimed invention, but not limit the invention to the examples provided below.

EXAMPLES

The stanol-fatty acid-esters of the invention were prepared by the acid catalyzed esterification reaction method as follows: stanol (10 mmol), fatty acid (12 mmol) and sodium bisulfate (0.12 mmol) were stirred neat under vacuum for 16 hours, at 150° C. The resulting stanol-ester products were isolated using either the technique described above as Method A (employing both water and an organic solvent) or Method B (an aqueous separation process). When glass-like products were formed in method A, they were converted into free flowing solids upon cooling below 0° C. Gas chromatography analysis of crude reaction product indicated that the reactions proceed to greater than 95% completion. Final work-up was performed according to methods A or B as described above.

Analytical data for five representative stanol-esters are described below. Analytical data for an ester of cholestanol, as an additional model is also included.

Example 1

β-Sitostanol Stearate was produced by the reaction of β-sitostanol and stearic acid. NaHSO$_4$ was used as the catalyst and the stigmastanol stearate was isolated using Method A described above.

The analytical results for the isolated stigmastanol stearate was as follows:

$^1$HNMR (CDCl$_3$): (4.60(quintet, 1H), 2.19(t, 8, 2H), 1.88(d, 12, 1H); IR (cm$^{-1}$, KBr): 1739(s, C=O), 1454(m), 1388(m), 1182(s, C—O), 725(m); Elemental Analysis for C$_{47}$H$_{86}$O$_2$: calculated: C, 82.55%; H, 12.59%, found: C, 82.70%; H, 12.50%; Melting Point (DSC): 103–105° C.

Example 2

β-Sitostanol Stearate was produced by the reaction of β-sitostanol and stearic acid. NaHSO$_4$ was the catalyst used and the stigmastanol stearate was isolated using Method B as described above.

The analytical results of the isolated compound is presented below:

$^1$HNMR (CDCl$_3$): (4.62, quintet, 1H), 2.18(t, 8, 2H), 1.88(d, 12, 1H); IR (cm$^{-1}$, KBr): 1739(s, C=O), 1467(m), 1381(m), 1176(s, C—O), 718(m); Elemental Analysis for C$_{47}$H$_{86}$O$_2$: calculated: C, 82.55%; H, 12.59%; found: C, 82.31%; H, 12.63%; MP (DSC): 101–104° C.; % H$_2$O (Karl Fischer) 0.73%.

Example 3

β-Sitostanol Palmitate was produced by the reaction of β-sitostanol and palmitic acid. NaHSO$_4$ was employed as a catalyst and the stigmastanol palmitate was isolated using the procedure described above as Method A. The analytical results of the isolated stigmastanol palmitate is presented below:

$^1$HNMR (CDCl$_3$): (4.68(quintet, 1H), 2.24(t, 8, 2H), 1.95(d, 12, 1H); IR (cm$^{-1}$, KBr): 1739(s, C=O), 1460(m), 1394(m), 1176(s, C—O), 725(m); Elemental Analysis for C$_{45}$H$_{82}$O$_2$: calculated: C, 82.57%; H, 12.54%; found: C, 82.59%; H, 12.53%; Melting Point (DSC): 102–104° C.

Example 4

β-Sitostanol Oleate was produced by the reaction of β-sitostanol and oleic acid. NaHSO$_4$ was employed as a catalyst and the stigmastanol oleate was isolated using the technique described as Method B. The analytical results are presented below:

$^1$HNMR (CDCl$_3$): (5.27(m, 2H), 4.62(quintet, 1H), 2.23 (t, 8, 2H); IR (cm$^{-1}$, neat): 1739(s, C=O), 1461(m), 1387 (m), 1176(s, C—O), 1010(m), 718(m); Elemental Analysis for C$_{47}$H$_{84}$O$_2$: calculated: C, 82.80%; H, 12.33%; found: C, 82.98%; H, 12.36%; Melting Point (DSC): 41–44° C.

Example 5

Cholestanol Oleate was produced by the reaction of cholestanol and oleic acid. NaHSO$_4$ was used as a catalyst and the cholestanol oleate was isolated using the technique described as Method A. The analytical results are presented below:

$^1$HNMR (CDCl$_3$): (5.30(m, 2H), 4.65(quintet, 1H), 2.22 (t, 8, 2H); IR (cm$^{-1}$, neat): 1725(s, C=O), 1454(s), 1367 (m), 1168(m, C—O), 1003(m), 711(m); Elemental Analysis for C45H80O2: calculated: C, 82.67%; H, 12.25%; found: C, 82.64%; H, 12.34%; Melting Point (DSC): 20–25° C.

Comparative Example

The reaction of canola oil and stanol by an interesterification route provides a product mixture having the following approximate, non-reproducible distribution by weight:

Stanol-oleate 67%

Stanol-linoleate 19%

Stanol-linolenate 9%

Stanol-palmitate 3%.

Example 6

A reaction was carried out using a oleic acid with a 1.05 molar excess and stanols with 0.2% of sodium bicarbonate as a catalyst. Addition of 0.2% activated carbon was added before the reaction was started. The material was heated to 165° C. and water started was observed in the condenser. The reaction was heated to 170° C. when the fatty acids levels had stopped falling water was added and separated from the mixture. The color of the product was then read as about 8 on the Gardner scale.

Example 7

Example 6 was repeated without the carbonand the color of the washed product was 11+.

Example 8

Example 6 was repeated using 0.2% of zinc oxide as the catalyst. The product had a color of 9 on the Gardner scale. Examples 9 and 10 demonstrate the ease of employing the color deactivating agent in the present invention. Further color improvements can be readily obtained by modifying the amount of the color deactivating agent employed as well as other process variables.

Example 9

The reaction used in Example 6 was repeated without a catalyst No reaction took place until the temperature was over 200° C. and required more than 10 hours at 235° C. or higher reaction temperatures to complete the reaction. This demonstrates the benefits of the catalysts described herein, thereby allowing the reaction to proceed at lower temperatures and at a faster rate.

We claim:

1. A method for producing stanol/sterol-esters comprising:

providing a stanol/sterol of the formula:

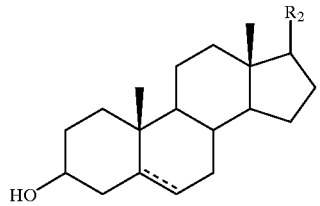

providing an acid, reacting said stanol/sterol and acid in the presence of a sufficient amount of catalyst and a sufficient amount of a color deactivating agent to form the substantially discrete corresponding stanol/sterol ester of the formula:

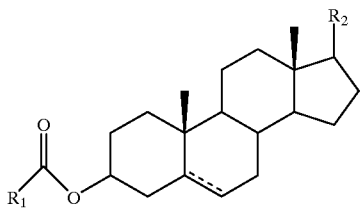

wherein $R_1$ is a carbon chain having a length of from about $C_5$–$C_{25}$, and $R_2$ is a carbon chain having a length of from about $C_3$–$C_{15}$.

2. The method of claim 1 wherein the reaction is conducted neat, with the acid acting as the solvent.

3. The method of claim 1 wherein the catalyst is basic in water.

4. The method of claim 3 wherein the catalyst is zinc oxide.

5. The method of claim 1 wherein the corresponding stanol/sterol ester is provided in an amount not less than about 98% by weight.

6. The method of claim 1 wherein $R_1$ of the stanol/sterol-ester has a value of from about from $C_{12}$ to $C_{21}$.

7. The method of claim 1 wherein the reaction temperature is from about 100 to about 220° C.

8. The method of claim 1 wherein the reaction is run under vacuum.

9. The method of claim 1 wherein the isolation of the corresponding stanol/sterol-ester is performed in a completely aqueous process.

10. The process of claim 1 wherein the color deactivating agent is charcoal or activated carbon.

11. The process of claim 1 wherein the amount of color deactivating agent is from about 0.05 to about 1 weight percent based upon the reaction total weight.

12. A method for producing stanol/sterol-esters comprising: providing a stanol/sterol of the formula:

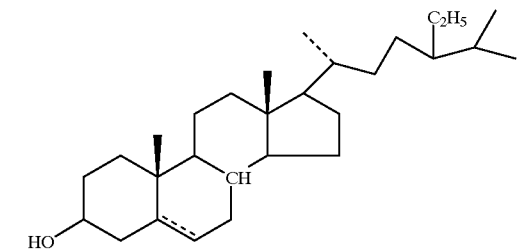

providing a polyunsaturated fatty acid having from $C_6$ to $C_{24}$ carbon atoms in length;

reacting said stanol/sterol and fatty acid in the presence of a sufficient amount of catalyst and an effective amount of a color deactivating agent, resulting in the production of the substantially discrete corresponding stanol/sterol-ester.

13. The method of claim 12 wherein the reaction is conducted neat, with the polyunsaturated fatty acid acting as the solvent.

14. The method of claim 12 wherein the catalyst is a Lewis acid.

15. The method of claim 14 wherein the Lewis acid is zinc oxide.

16. The method of claim 12 wherein the corresponding stanol/sterol-ester is provided in an amount of not less than about 98% by weight.

17. The method of claim 12 wherein the reaction temperature is from about 100 to about 220° C.

18. The method of claim 12 wherein the reaction is run under vacuum.

19. The method of claim 12 wherein the isolation of the corresponding stanol/sterol-ester is performed in a completely aqueous process.

20. A method for producing stanol/sterol-esters comprising:

providing a stanol/sterol of the formula:

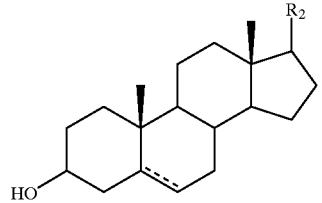

providing an acid, reacting said stanol/sterol and acid in the presence of a sufficient amount of Lewis acid catalyst; and optionally a sufficient amount of a color deactivating agent to form the substantially discrete corresponding stanol/sterol ester of the formula:

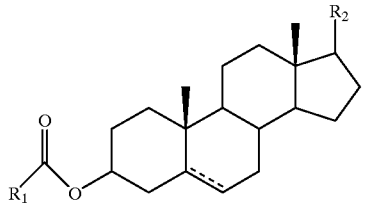

wherein $R_1$ is a carbon chain having a length of from about $C_3$–$C_{24}$, and $R_2$ is a carbon chain having a length of from about $C_3$–$C_{15}$.

* * * * *